US00PP27888P3

(12) United States Plant Patent
Van Dijk

(10) Patent No.: US PP27,888 P3
(45) Date of Patent: Apr. 11, 2017

(54) ***ANTHURIUM* PLANT NAMED 'ANTHIOWIR'**

(50) Latin Name: ***Anthurium andreanum* L.**
Varietal Denomination: ANTHIOWIR

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 43 days.

(21) Appl. No.: 14/545,922

(22) Filed: Jul. 8, 2015

(65) Prior Publication Data

US 2017/0013764 P1 Jan. 12, 2017

(51) Int. Cl.
*A01H 5/02* (2006.01)

(52) U.S. Cl.
USPC ..... Plt./368

(58) Field of Classification Search
USPC ..... Plt./368, 365, 369, 367
See application file for complete search history.

(56) References Cited

PUBLICATIONS

Anthura Unlimited in Varieties *Anthurium* catablogue 2016-2017, retrieved on Oct. 17, 2016, retrieved from the Internet at <https://www.anthura.nl/wp-content/uploads/2016/05/Anthurium_LORES.pdf> pp. 42 and 60.*

New Plants and Flowers Two new and two improved cut *anthuriums* 2014, retrieved on Oct. 17, 2016, retrieved from the Internet at <http://www.newplantsandflowers.com/two-new-and-two-improved-cut-anthuriums/> 2 pp.* www.newplantsandflowers.com/two-new-and-two-improved-cut-anthuriums/, published May 30, 2014, 2 pages, retrieved from the internet on Dec. 12, 2016.

EU Community Plant Variety Rights Application No. 2014/1582, Application n°A201403995, filed Jun. 10, 2014, 7 pages.

EU Community Plant Variety Office Official Gazette, Apr. 2014, Aug. 15, 2014, cover page and pp. 28, 47.

Anthura *Anthurium* catalogue: Cut flower and pot plant 2015/2016, published May 2015, cover page and pp. 25, 57.

* cited by examiner

*Primary Examiner* — June Hwu
(74) *Attorney, Agent, or Firm* — Jondle & Associates, P.C.

(57) ABSTRACT

A new and distinct variety of *Anthurium* plant named 'ANTHIOWIR' particularly distinguished by having a characteristic glossy, purple spathe and a deep purple spadix, elliptical cordate and dark green leaves with dark red primary veins, continuously flowering throughout the year, little shoots creating an open plant habit with a height of 55 cm to 65 cm, is disclosed.

3 Drawing Sheets

Genus and species: *Anthurium andreanum* L.
Variety denomination: 'ANTHIOWIR'.

BACKGROUND OF THE NEW PLANT

The present invention comprises a new and distinct variety of *Anthurium*, botanically known as *Anthurium andreanum* L., and hereinafter referred to by the variety name 'ANTHIOWIR'. The new variety originated from a hybridization made in July 2000 in Bleiswijk, The Netherlands. The female parent was a pink-purple *Anthurium* pot plant designated '372-01' (unpatented), and the male parent was a purple *Anthurium* plant designated '2305-01' (unpatented).

A single plant was selected in August 2002 and has been asexually reproduced repeatedly by meristem tissue culture in Bleiswijk, The Netherlands over a seven-year period. The present invention has been found to retain its distinctive characteristics through successive asexual propagations.

Plant Breeder's Rights for this variety have been applied for in the European Union on Jun. 10, 2014 and in China on Jan. 29, 2015. 'ANTHIOWIR' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Purple and glossy spathe;
2) Deep purple spadix;
3) Brown-red peduncle;
4) Elliptical cordate leaf with dark red veins; and
5) Dark green foliage.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 58-week old plant grown in a greenhouse in Bleiswijk, The Netherlands in June 2015.

DESCRIPTION OF THE NEW VARIETY

Figure 1:
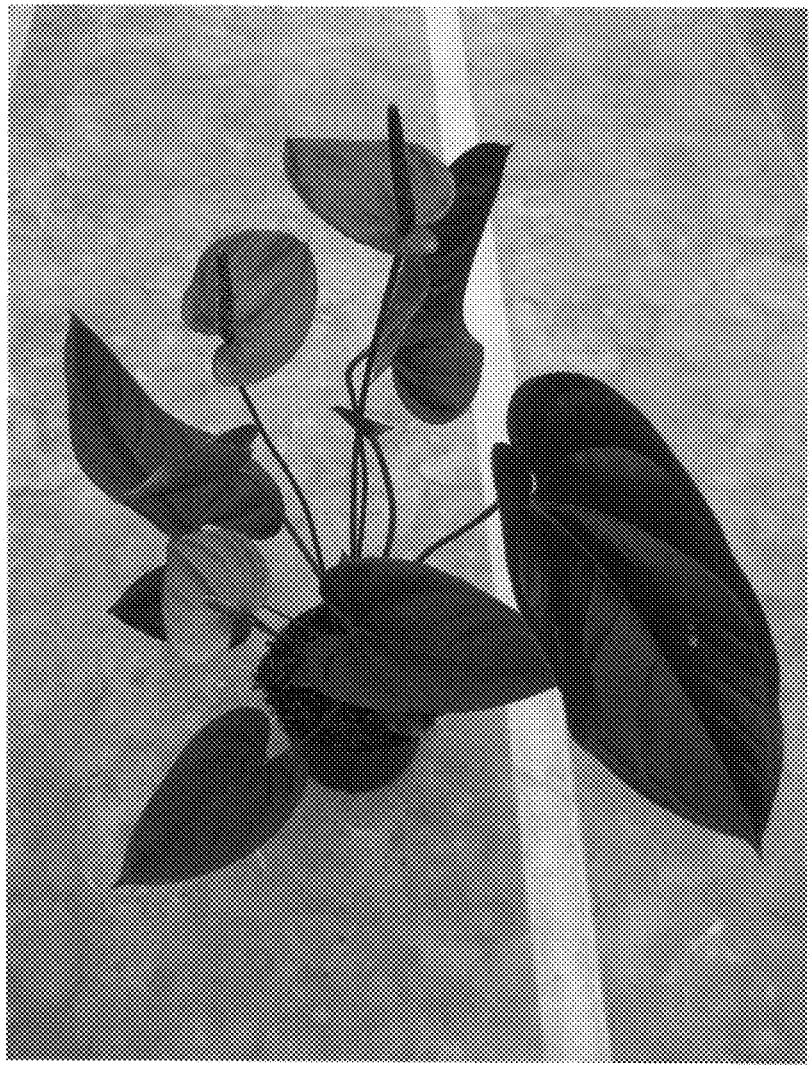
FIG. 1 shows the overall plant habit, including blooms and foliage.
Figure 2:
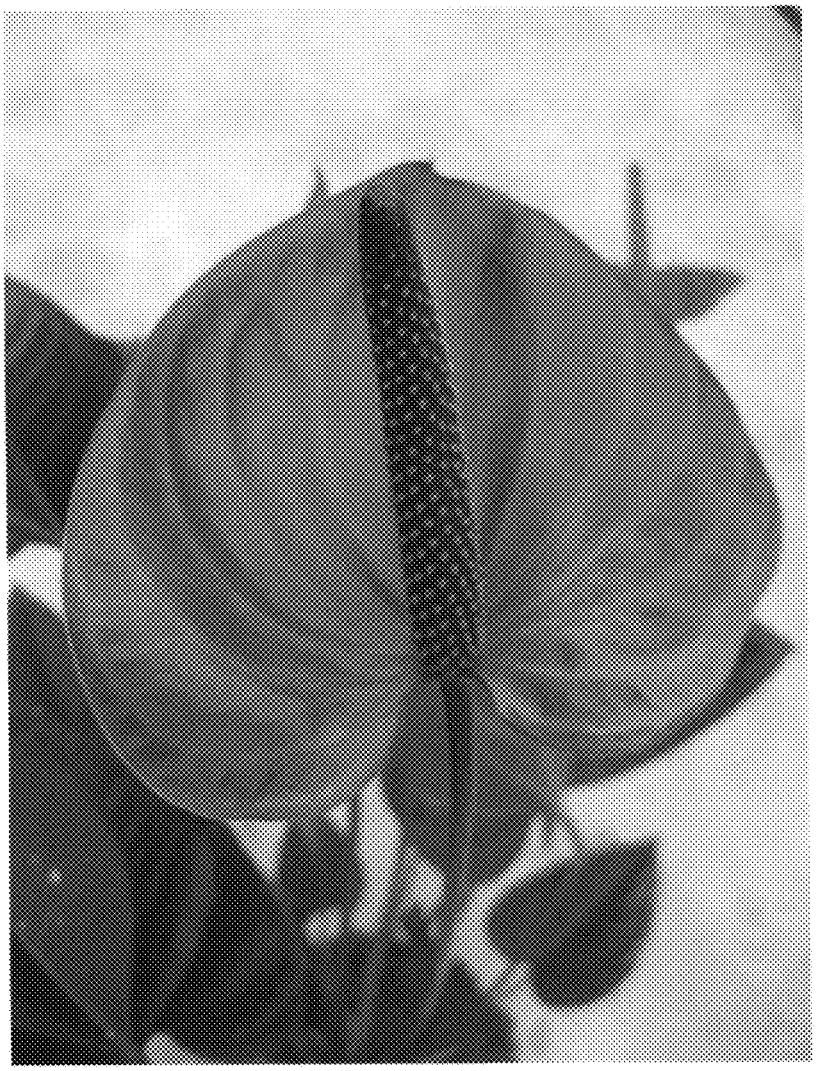
FIG. 2 shows a close-up of the mature spathe.
Figure 3:
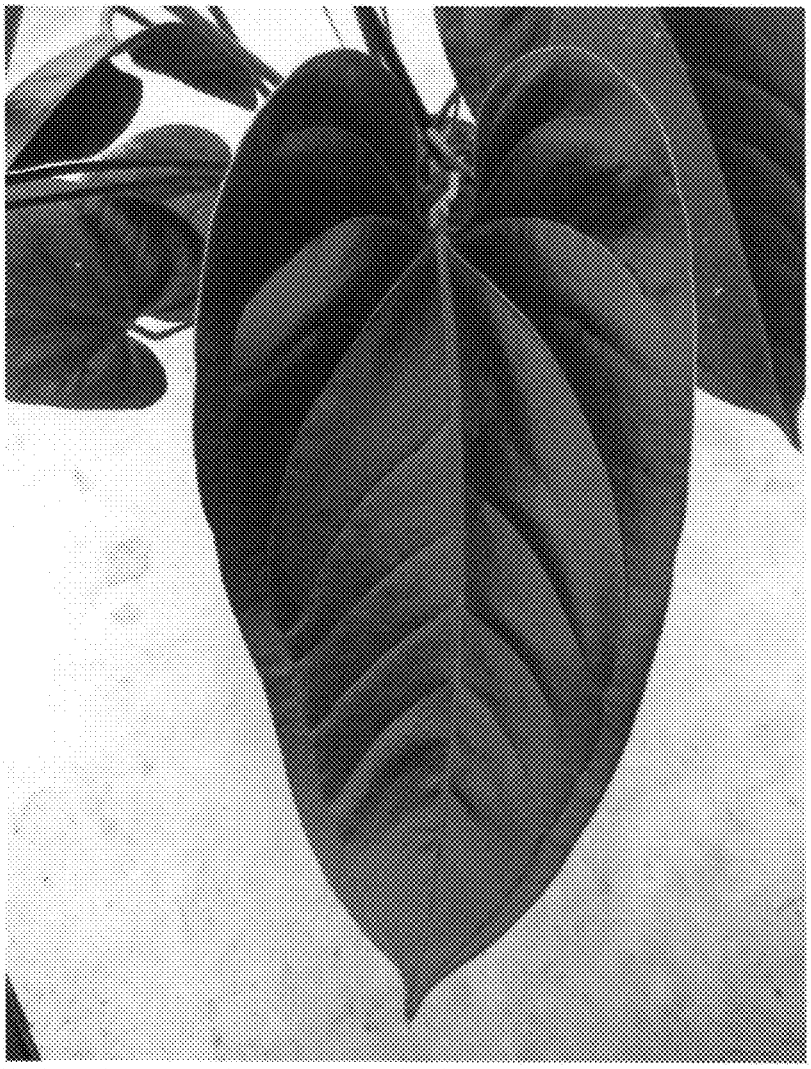
FIG. 3 shows the upper leaf blade surface.

The following detailed description sets forth the distinctive characteristics of 'ANTHIOWIR'. The data which define these characteristics were collected from asexual reproductions carried out in Bleiswijk, The Netherlands. The plant history was taken on 58-week old plants which were planted from tissue culture in 17-centimeter pots and grown in a glass greenhouse between 19° C. and 24° C. Observations were made in June 2015. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHIOWIR'.

Parentage:

*Female parent*.—*Anthurium* plant '372-01' (unpatented).

*Male parent*.—*Anthurium* plant '2305-01' (unpatented).

Plant:

*Propagation*.—Meristem tissue culture.

*Root description*.—Fleshy white-cream colored roots with small hairy lateral roots having yellow-colored root tips.

*Time to produce a finished flowering plant*.—50 to 60 weeks for a full-grown, cutflower plant.

*Growth habit*.—Herbaceous perennial.

*Height* (*measured from soil, including inflorescence*).—55.0 cm to 65.0 cm.

*Width* (*measured from leaf tips*).—50.0 cm to 60.0 cm.

Leaves:

*Immature leaves*.—Length: 21.0 cm to 24.0 cm. Width: 13.0 cm to 15.0 cm. Color: Upper surface: RHS 147A. Lower surface: RHS 146A. Texture (both upper and lower surfaces): Shiny.

*Mature leaves*.—Length (fully expanded): 26.0 cm to 29.0 cm. Width: 15.0 cm to 17.0 cm. Shape: Elliptical cordate. Apex: Acuminate. Base: Cordate. Leaf blade angle with the petiole: Between 110 degrees and 140 degrees. Leaf margin: Entire. Color: Upper surface: RHS 139A. Lower surface: RHS 146A. Texture: Shiny, leathery and thick. Venation: Pinnate veining; the mid-vein and primary veins (the veins that radiate out from the junction of petiole and leaf) protrude at the underside of the leaf blade. Venation color: Upper surface: Dark red (RHS 183A) at the base and yellow-green (RHS 146B) towards the leaf tip (mid-vein); dark red (RHS 183B) at the base and yellow-green (RHS 146B) towards the leaf tip (primary veins). Lower surface: RHS 152A (mid-vein) and RHS 183B (primary veins).

*Lobes*.—Arrangement: Non-touching. Length of lobes of mature leaf blades: 4.0 cm to 5.0 cm. Width of lobes of mature leaf blades: 6.0 cm to 7.0 cm. Distance for petiole/leaf junction to highest point on lobes of mature leaf blades: 5.0 cm to 7.0 cm.

*Petiole*.—Cross-section: Round. Diameter: 0.4 cm to 0.5 cm. Length: 28.0 cm to 35.0 cm for a mature leaf size. Color: Mature leaf: RHS 200C to 200D. Immature leaf: RHS 144A. Cataphyll color surrounding the petiole: Outside: RHS 144A (after some time the apex changes into RHS 181B). Inside: RHS 145C.

*Geniculum*.—Length: 3.0 cm to 4.0 cm. Width: 0.5 cm to 0.6 cm. Color: RHS 166B to 166C.

Inflorescence:

*Arrangement*.—Single.

*Flowering habit* (*length of flowering season*).—Continuous.

*Number of inflorescences per plant*.—2 to 4.

*Fragrance*.—Absent.

*Longevity of inflorescence on plant*.—35 to 40 weeks.

*Longevity of the flower as a cut flower*.—30 to 40 days.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 100 degrees and 120 degrees; the spathe stands on a wiry peduncle about 17.0 cm to 20.0 cm above the foliage.

*Shape*.—Cordate.

*Apex*.—Acuminate.

*Base*.—Cordate.

*Texture*.—Shiny and smooth.

*Margin*.—Entire.

*Size*.—Length: 10.0 cm to 12.0 cm. Width: 10.0 cm to 12.0 cm.

*Color*.—Just fully open: Upper surface: RHS 71A (discolors after some time to red-purple (RHS 59A) and yellow green lobes (RHS 146B)). Lower surface: RHS 77A.

Peduncle:

*Shape*.—Erect.

*Cross-section*.—Round.

*Length*.—40.0 cm to 50.0 cm.

*Diameter*.—0.3 cm to 0.5 cm.

*Color*.—RHS 183A.

Flowering time:

*General*.—One small rooted untreated tissue culture plant of 4.0 cm tall will flower after 6 to 8 months, depending on the season, and 1 blossom appears at a time. More blossoms appear successively after every 6 to 10 weeks so that there is a continuous production of cutflowers. Smaller blossoms may occur on less mature plants.

Spadix:

*Size*.—Length: 6.0 cm to 8.0 cm (depending on flower size). Width (at apex): 0.5 cm to 0.7 cm. Width (at base): 0.9 cm to 1.1 cm.

*Shape*.—Columnar.

*Angle from spadix tip to peduncle*.—150 to 170 degrees.

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 79A. Mature: RHS 79A.

Flowers:

*Quantity per spadix*.—210 to 280.

*Spadix flower arrangement*.—Bisexual, rounded in cross-section.

*Shape*.—Rounded.

*Size*.—Length: 0.05 cm to 0.1 cm. Diameter (maximum): 0.1 cm.

*Color*.—RHS 79D.

Reproductive organs:

*Stamens*.—Not visible.

*Pollen amount*.—Many.

*Pollen color*.—RHS 156D.

*Pistil*.—Quantity: Many. Length: Less than 0.01 cm. Color: RHS 79D.

*Style*.—Not observed.

*Stigma*.—Shape: Ovoid. Diameter: Less than 0.01 cm. Color: RHS 79D.

*Ovary*.—Rarely visible.

*Ovary color*.—Not measured.

Fruit and seed set: None observed.

Disease and pest resistance: Not observed to date.

COMPARISON WITH PARENTAL AND COMMERCIAL VARIETIES

'ANTHIOWIR' differs from the female parent plant '372-01' (unpatented) in that 'ANTHIOWIR' has a purple spathe, whereas '372-01' has a purple-pink spathe.

'ANTHIOWIR' differs from male parent plant '2305-01' (unpatented) in that 'ANTHIOWIR' has a cordate spathe, whereas '2305-01' has a lanceolate spathe.

'ANTHIOWIR' differs from commercial variety 'ANTHIMODI' (unpatented) in that 'ANTHIOWIR' has a purple spadix, whereas 'ANTHIMODI' has a white spadix with a yellow tip. Additionally, 'ANTHIOWIR' has a smaller spathe width than 'ANTHIMODI'.

'ANTHIOWIR' differs from commercial variety 'ANTHARXI' (unpatented) in that 'ANTHIOWIR' has a cordate spathe shape, whereas 'ANTHARXI' has an ovate spathe shape. Additionally, 'ANTHIOWIR' has a larger spathe width than 'ANTHARXI'.

I claim:

1. A new and distinct variety of *Anthurium* plant named 'ANTHIOWIR', substantially as illustrated and described herein.

* * * * *